(12) United States Patent
Reuvekamp et al.

(10) Patent No.: US 8,278,384 B2
(45) Date of Patent: Oct. 2, 2012

(54) POLYMER COMPOSITION

(75) Inventors: Louis-Philippe Antoine Eugène Maria Reuvekamp, Enschede (NL); Gerard Nijman, Losser (NL); Ewout Feenstra, Utrecht (NL)

(73) Assignee: Apollo Vredestein B.V., Enschede (NL)

( * ) Notice: Subject to any disclaimer, the term of this patent is extended or adjusted under 35 U.S.C. 154(b) by 353 days.

(21) Appl. No.: 12/516,033

(22) PCT Filed: Nov. 23, 2007

(86) PCT No.: PCT/NL2007/050586
§ 371 (c)(1),
(2), (4) Date: Dec. 2, 2009

(87) PCT Pub. No.: WO2008/063065
PCT Pub. Date: May 29, 2008

(65) Prior Publication Data
US 2010/0081761 A1    Apr. 1, 2010

(30) Foreign Application Priority Data

Nov. 23, 2006   (NL) .................................. 20000330

(51) Int. Cl.
*C08L 9/00* (2006.01)
(52) U.S. Cl. .................. 524/451; 524/571; 524/588
(58) Field of Classification Search .............. 524/451, 524/571, 588
See application file for complete search history.

(56) References Cited

U.S. PATENT DOCUMENTS

| | | | |
|---|---|---|---|
| 2,304,263 A | 9/1938 | Luty | |
| 3,344,105 A | 9/1967 | McDonel et al. | |
| 4,517,146 A | 5/1985 | Takasu et al. | |
| 5,594,052 A | 1/1997 | D'Sidocky et al. | |
| 6,279,633 B1 | 8/2001 | Corvasce | |
| 6,765,045 B1 * | 7/2004 | Daniel et al. | 524/237 |
| 2004/0175527 A1 | 9/2004 | Shiota et al. | |
| 2005/0017541 A1 | 1/2005 | Jungert | |

FOREIGN PATENT DOCUMENTS

| | | |
|---|---|---|
| EP | 0 518 194 | 12/1992 |
| EP | 1 061 097 | 12/2000 |
| EP | 1 072 442 | 1/2001 |
| FR | 2 454 899 | 11/1980 |
| JP | 07 096562 | 4/1995 |
| NL | 6 613 607 | 3/1967 |
| WO | 2005/105854 | 11/2005 |
| WO | WO 2005/105854 A2 * | 11/2005 |
| WO | 2008/063066 | 5/2008 |
| WO | 2008/063067 | 5/2008 |

OTHER PUBLICATIONS

International Search Report from corresponding International Application No. PCT/NL2007/050586 mailed Feb. 28, 2008.
International Preliminary Report on Patentability from corresponding International Application No. PCT/NL2007/050586 mailed Feb. 20, 2009.
International Search Report from related International Application No. PCT/NL2007/050587 mailed Feb. 26, 2008.
International Preliminary Report on Patentability from related International Application No. PCT/NL2007/050587 mailed Mar. 3, 2009.
International Search Report from related International Application No. PCT/NL2007/050588 mailed Feb. 21, 2008.
International Preliminary Report on Patentability from related International Application No. PCT/NL2007/050588 mailed Jan. 20, 2009.

* cited by examiner

*Primary Examiner* — Robert D. Harlan
(74) *Attorney, Agent, or Firm* — Renner, Otto, Boisselle & Sklar, LLP

(57) ABSTRACT

The invention relates to a polymer composition comprising a matrix polymer, silica particles dispersed therein, and a coupling agent and a screening agent for the silica particles, and is characterized in that the screening agent is an alkylamine compound. The polymer composition is particularly suitable for the manufacture of rubber tires with improved rolling resistance.

17 Claims, No Drawings

POLYMER COMPOSITION

This application is a national phase of International Application No. PCT/NL2007/050586 filed Nov. 23, 2007 and published in the English language, and claims priority to NL 2000330 filed Nov. 23, 2006.

The invention relates to a polymer composition comprising a matrix polymer, silica particles dispersed therein, and a coupling agent and a screening agent for the silica particles. The invention also relates to moulded articles manufactured with the polymer composition, and in particular rubber tyres.

In recent years silica has increasingly been applied as strengthening filler in polymer compositions, and particularly in rubber compositions for tyre treads. Compared to the also frequently applied soot, silica generally improves the rolling resistance of tyres considerably. Soot can be admixed relatively easily into rubber, among other reasons because both are hydrophobic substances. A good admixing of silica into usual rubbers, and in particular into non-polar rubbers, is however particularly difficult because the silica particles readily form agglomerates, among other reasons due to hydrogen bridge-forming between the silica particles. There is hereby the chance of the silica particles not being properly dispersed in the rubber matrix, which generally results in relatively poor dynamic and mechanical properties of the rubber composition in question. In order to obviate this, it is known to modify the silica surface, whereby the compatibility of the silica particles with the rubber matrix is increased. Coupling agents, such as for instance bifunctional organosilane compounds, are generally applied for this purpose. Such coupling agent enhance the interaction with the rubber matrix. It is assumed that this improved interaction is brought about by a first reaction which bonds the organosilane compound to the silica surface, and a second reaction which bonds the organosilane compound to the rubber matrix by means of suitable functional groups provided for this purpose. Although the invention is by no means limited hereto, a coupling agent frequently applied in rubber compositions for tyre treads is bis-(triethoxysilylpropyl)tetrasulphide (TESPT).

It is likewise usual to cover the part of the silica surface which has not reacted with the coupling agent, or only partly so, by means of suitable screening agent. Silica particles with insufficiently screened surface can again form agglomerates in the course of time, which results in an undesirable stiffening of the polymer composition. A usual compound in this respect is for instance diphenyl guanidine (DPG), which enters into a substantially physical interaction with the silica surface. The DPG also ensures that the polymer composition becomes more basic in that the "acidic" silica is screened.

The existing screening agents, such as for instance DPG, have the drawback however that they relatively easily cause discolouration under the influence of UV radiation.

The present invention therefore has for its object to provide a polymer composition, and in particular a rubber composition, which can be coloured well and which displays reduced discolouration under the influence of UV radiation relative to the known polymer composition and also has, and preferably also retains, good dynamic/mechanical properties.

This object is achieved according to the invention by a polymer composition according to the preamble of claim 1, wherein the screening agent is an alkylamine compound. It has been found that such a polymer composition not only ensures an enduringly good dispersion of the silica particles incorporated therein, but that discolouration due to UV radiation is moreover prevented to a great extent. A further advantage of the polymer composition according to the invention is that it can be coloured well. In order to make coloured objects from a polymer, and in particular from rubber, which are moreover UV-stable—i.e. do not discolour and/or deteriorate mechanically under the influence of UV radiation—the polymer composition must generally first be made almost wholly white. The choice of the active filler is very decisive here. In the case of a filler which improves rolling resistance it must be noted that, in order to make a rubber composition white, use could heretofore only be made of silica particles in combination with a coupling agent. The invented screening agent reduces the drawbacks associated with the use of silica particles, whereby the advantages of using silica particles, such as good colouring ability, can be utilized.

The polymer composition according to the invention is preferably characterized in that the alkylamine does not comprise any unsaturated alkyl groups. This measure further increases the resistance to discolouration under the influence of UV radiation. The polymer composition is even more preferably characterized in that the alkylamine comprises a heterocyclic amine. Owing to the non-polar character of the cyclic aliphatic groups a further improved miscibility with the rubber matrix polymer is achieved. It is further advantageous when the polymer composition is characterized in that it is substantially free of guanidine, and in particular of diphenyl guanidine.

In a further preferred variant of the polymer composition according to the invention the screening agent is an alkylamine compound according to the following formula (1):

in which R1, R2 or R3 are an H atom and/or an aliphatic group.

Compounds according to formula 1 can be primary, secondary or tertiary amine compounds with respectively 1, 2 or 3 aliphatic groups. The compound is preferably a secondary amine, wherein R3 is an H atom and R1 and R2 are aliphatic groups. According to the invention the amine according to formula (1) can react with the surface of the silica particles and/or enter into a physical interaction via the amine group. With a suitable choice of the aliphatic groups of the amine according to formula (1) the polarity of the amine can be adjusted optimally so that the miscibility with the matrix polymer is improved further. It is advantageous here when the alkylamine comprises a heterocyclic amine. Such compounds are commercially available but are not known as screening agent in polymer compositions, particularly rubber compositions, and still more particularly rubber compositions comprising silica particles. A polymer composition which is particularly favourable in respect of the miscibility with matrix polymers comprises a heterocyclic amine, and in particular a dicycloalkylamine, as screening agent for the silica particles. Even more preferably a dicyclohexylamine is applied as heterocyclic amine.

The molecular weight of the alkylamine according to the invention can be selected within broad limits. It has however been found that the screening agent acts extremely well when the number average molecular weight (Mn) lies between 20 and 1000 g/mol, preferably between 50 and 500 g/mol, most preferably between 100 and 300 g/mol.

The silica particles applied in the polymer composition according to the invention can in principle comprise of any known type. It is also possible to apply mixtures of different types. The silica particles preferably have a CTAB-specific surface area lying between 50 and 250 m$^2$/g, more preferably between 90 and 210 m$^2$/g, and most preferably between 120 and 180 m$^2$/g. The CTAB-specific surface area is measured according to a method known to the skilled person using adsorption by cetyl trimethyl ammonium bromide. Nor is the particle size distribution of the silica particles in principle limited to specific limits. Suitable silica particles are for instance substantially built up of primary particles with an average particle size of about 30 nm, agglomerates of silica particles with an average size of several hundred nm, and aggregates of silica particles with an average size of about 10 μm. The average particle size of the silica particles preferably lies between 0.1 and 50 μm, more preferably between 1 and 30 μm. If desired, the particle size distribution of the silica particles can be modified, for instance by sieving and/or grinding the silica particles.

The polymer composition according to the invention can be prepared in a manner known to the skilled person. Any known method of mixing polymers, fillers and other additives is in principle suitable for this purpose. It is thus possible to mix the matrix polymer, the silica particles, the coupling agent and/or the screening agent, supplemented with other additives and/or polymers if desired, using an internal mixer or Banbury mixer, a single or double-screw extruder apparatus, a blade kneader, a Buss Co-kneader, a roller and the like. Suitable temperatures during mixing are substantially determined by the rheological properties of the matrix polymer.

The quantity of screening agent added to the polymer composition can in principle be selected within broad limits. The polymer composition is preferably characterized in that it comprises 0.1-10% by weight of screening agent relative to the total weight of the polymer composition. This is more preferably 0.5-5% by weight of screening agent relative to the total weight of the polymer composition, and most preferably 1-3% by weight of screening agent relative to the total weight of the polymer composition.

The matrix polymer applied in the polymer composition according to the invention can be selected from the known polymers. Suitable matrix polymers are for instance chosen from the group formed by polystyrene and copolymers of styrene with acrylonitrile, polyamides, polyesters, polyacrylates, polychlorides and polycarbonates. Particularly suitable matrix polymers comprise a rubber polymer. The rubber polymer preferably applied in the polymer composition according to the invention can be selected from the known rubbers. In general these rubbers have a glass transition temperature Tg lower than −10° C., although this is not essential. Rubbers suitable for application are for instance chosen from the group of natural rubbers, isoprene rubbers, butadiene rubbers, styrene butadiene copolymer rubbers, acrylonitrile butadiene copolymer rubbers, if desired copolymerized with styrene, butadiene isoprene copolymer rubbers, chloroprene rubbers, butyl and acryl rubbers, and ethylene-propylene copolymers which, if desired, comprise a third copolymerizable diene monomer such as for instance 1,4-hexadiene, dicyclopentadiene, dicyclooctadiene, methylene norbornene, ethylidene norbornene and tetrahydroindene. If desired, the rubber polymer also comprises a minor quantity of natural rubber and/or elastomer, which is preferably composed of 1,3-diene compounds such as for instance butadiene and/or isoprene and/or 2,3-dimethyl butadiene. The rubber polymer applied as matrix polymer in the polymer composition is preferably an ethylene-propylene rubber, the applied rubber polymer is more preferably an ethylene-propylene-diene rubber (EPDM). Mixtures of said rubber polymers are likewise possible.

A cross-linker for the rubber polymer can be added if desired. Particularly suitable cross-linkers for the rubber polymer, in particular for the EPDM rubber polymer, comprise phenol resins in combination with a tin chloride compound as catalyst. In addition, it is also possible to apply cross-linkers on the basis of sulphur and/or peroxides. The cross-linker for the rubber polymer is preferably added only after the reactions and/or physical interactions of coupling agent and/or screening agent with the surface of the silica particles have at least partly taken place, so for instance at the end of the extruding device, if this is applied as mixing apparatus for the preparation of the polymer composition. If desired, the matrix polymer can also be provided with reactive groups such as for instance hydroxyl groups, alkoxysilyl groups, amino and epoxide groups and/or carboxyl groups. Particularly suitable matrix polymers are those provided with carboxyl groups, for instance by grafting unsaturated dicarboxylic anhydride compounds onto the rubber polymer. A maleic anhydride-functionalized rubber polymer is particularly suitable as matrix polymer.

Within the scope of the present invention the matrix polymer is understood to mean the polymer which substantially determines the composition and properties of the polymer composition and to which other polymers, compounds and/or fillers can be added if desired. The relative weight ratios of the constituents of the polymer composition can herein be selected within broad limits. The polymer composition according to the invention preferably comprises 30-70% by weight of matrix polymer, 15-45% by weight of silica particles, 1-3% by weight of coupling agent and 1-3% by weight of screening agent relative to the total weight of the polymer composition, wherein the remainder comprises the other additives.

If desired, additives can be added to the polymer composition according to the invention. Examples of usual additives are stabilizers, antioxidants, lubricants, fillers, dyes, pigments, flame retardants, conductive fibres and reinforcing fibres. Particularly in the case of rubber polymers the polymer composition can also comprise an oil as additive. It is also possible to apply petroleum plasticizers. Coupling agents suitable for the polymer composition according to the invention comprises silane compounds. Particularly suitable silane compounds comprise di- and tetrasulphides. The polymer composition can be processed into an object in a manner known to the skilled person, for instance by means of injection moulding or compression moulding.

The invention also relates to a moulded article manufactured from a polymer composition according to the invention. Particularly suitable moulded articles according to the invention comprise a rubber tyre, sealing profiles for doors and/or windows, and/or flexible bodywork components such as for instance a spoiler for a vehicle. A flexible spoiler preferably manufactured from the polymer composition according to the invention is for instance described in the American patent applications US 2005/0012359 and in US 2005/0017541, the content of which is expressly included here in the present application. The spoiler described herein comprises an airflow-conducting element and an operating element therefor. The airflow-conducting element is attached to the bottom of the bumper, is manufactured from a rubber polymer and can be moved in and out by means of the operating element. A resilient connection between airflow-conducting element and bumper holds the spoiler in the moved-in inoperative position. The operating member can for instance take the form of a number of inflatable bellows disposed on the rear side of the spoiler. When the inflatable bellows is inflated, the spoiler moves forward from the moved-in position to the moved-out position. A fibre-reinforced plastic rod provides for lateral guiding of the element. On the basis of the method according to the invention the spoiler can be decorated with black and/or coloured inserts, for instance in the form of laterally running strips. It will be apparent that the invention is not limited to particular forms, but that in principle any form is possible.

The present invention will now be further elucidated on the basis of the following example, without however being limited thereto.

EXAMPLE I AND COMPARATIVE EXPERIMENT A

Example I

Preparation of Polymer Composition

A mixture of an ethylene-propylene-diene rubber (EPDM, Keltan 514 from the DSM company) and the constituents stated in table 1 was prepared by mixing in a standard kneader for about 5 minutes, at an average temperature of about 150° C. The silica came from the Rhodia company, type Zeosil-1165 MP, with a CTAB-specific surface area of 155 m$^2$/g. A polysiloxane compound (bis-(triethoxysilylpropyl)tetrasulphide from the Degussa company) was used as coupling agent. A standard vulcanizing system on the basis of sulphur was added to the mixture.

The quantities given in table 1 are parts per hundred parts of EPDM rubber (phr). An equimolar calculation was performed of the quantity of dicyclohexylamine relative to the quantity of DPG.

TABLE 1

Polymer compositions

| Material | Example I | Comparative experiment A |
| --- | --- | --- |
| EPDM | 100 | 100 |
| Oil | 20 | 20 |
| Silica | 50 | 50 |
| Silane coupling agent | 3.5 | 3.5 |
| Zinc oxide | 5 | 5 |
| Stearic acid | 1 | 1 |
| Vulcanizing system | 10 | 10 |
| Diphenyl guanidine (DPG) | — | 2 |
| Dicyclohexylamine | 1.72 | — |

The thus obtained mixture was then rolled out and cooled by being subjected to a rolling process at about 50° C. Discs with a diameter of about 3 cm and 0.5 cm thickness were then stamped out of the thus obtained sheet-like and unvulcanized rubber composition in order to measure the Payne number. The Payne number of a polymer composition is a measure of the quantity of agglomerates in the composition. For this purpose the discs are placed between the conical plates of a Rheometer and subjected to an oscillating, rotating movement at a temperature of 100° C., a fixed frequency of 0.5 Hz and a shear amplitude of 0.56%. The thus measured storage modulus G' (the Payne number) is a measure of the presence of agglomerates of silica particles in the polymer composition. The higher the Payne number, the more aggregates and/or agglomerates occur in the polymer composition.

The sheet-like rubber composition was then vulcanized for about 12 minutes at a temperature of about 160° C. After completion of the vulcanization the plates were then cooled to room temperature.

The thus obtained plates of about 150×150×2 mm were then divided into test pieces and subjected to an ageing test. This ageing test comprised of exposure to UV radiation for 6 hours by holding the plates under a UV lamp of the OSRAM Ultra Vitalux Gur 53, 300 Watt type for the indicated time. The degree of discolouration was measured after this ageing. The results obtained are shown in table 2.

Comparative Experiment A

Preparation of Polymer Composition

In the same manner described as in Example 1a mixture was prepared of the same rubber as in Example I and the constituents stated in table 1 under "Comparative Experiment A". The thus obtained mixture was compression-moulded into plates under the same conditions as in Example I. The Payne number of the unvulcanized mixture was also determined. The plates were subjected to the ageing test as described in Example I.

Obtained Test Results

The Payne numbers for the polymer compositions according to Example I and Comparative Experiment A both amounted to 0.5 Mpa. This indicates a similar dispersion of the silica particles in the respective rubber compositions. The results of the UV discolouration measurement are given in table 2.

TABLE 2

Results of discolouration measurement

| | Comparative Experiment A | Example I |
| --- | --- | --- |
| A before | −0.2 | −0.2 |
| A after 6 hours of UV | −0.94 | −0.86 |
| B before | −1.05 | −1.05 |
| B after 6 hours of UV | 2.73 | 1.24 |
| C before | 1.07 | 1.07 |
| C after 6 hours of UV | 2.89 | 1.51 |

A in table 2 indicates the difference between red and green, wherein a more positive A indicates more red and a more negative A indicates more green. B indicates the difference between yellow and blue, wherein a more positive B indicates more yellow and a more negative B indicates more blue. Finally, C indicates the gloss, wherein a more positive C indicates more gloss and a more negative C indicates a greater dullness. The greater the difference between before and after 6 hours of exposure to UV light, the more discolouration has occurred. The results of table 2 show that the polymer composition according to the invention displays considerably less discolouration than the known polymer composition.

The invention claimed is:

1. Polymer composition comprising a matrix polymer, silica particles dispersed therein, and a coupling agent and a screening agent for the silica particles, wherein the screening agent comprises a secondary amine compound and the polymer composition is substantially free of guanidine.

2. Polymer composition as claimed in claim 1, wherein the secondary amine compound does not comprise any unsaturated alkyl groups.

3. Polymer composition as claimed in claim 1, wherein the matrix polymer is a rubber polymer.

4. Polymer composition as claimed in claim 3, wherein the rubber polymer is an ethylene-propylene-diene rubber (EPDM).

5. Polymer composition as claimed in claim 1, wherein the coupling agent comprises a silane compound.

6. Polymer composition as claimed in claim 1, comprising 0.1-10% by weight of screening agent relative to the total weight of the polymer composition.

7. Polymer composition as claimed in claim 1, comprising 0.5-5% by weight of screening agent relative to the total weight of the polymer composition.

8. Polymer composition as claimed in claim 1, comprising 1-3% by weight of screening agent relative to the total weight of the polymer composition.

9. Polymer composition as claimed in claim 1 further comprising usual additives chosen from the group of the crosslinkers, stabilizers, antioxidants, lubricants, fillers, dyes, pigments, flame retardants, conductive fibres, reinforcing fibres, oil and petroleum plasticizers.

10. Polymer composition as claimed in claim 1, comprising 30-70% by weight of matrix polymer, 15-45% by weight of silica particles, 1-3% by weight of coupling agent and 1-3% by weight of screening agent relative to the total weight of the polymer composition, wherein the remainder comprises other additives.

11. A method of making a polymer composition comprising adding a dicycloalkylamine compound as a screening agent for silica particles to a polymer composition, the polymer composition comprising a matrix polymer, silica particles dispersed therein, and a coupling agent, wherein the polymer composition is substantially free of guanidine.

12. Moulded article manufactured from the polymer composition as claimed in claim 1.

13. Rubber tire manufactured from the polymer composition as claimed in claim 1.

14. Sealing profile manufactured from the polymer composition as claimed in claim 1.

15. Flexible spoiler for a vehicle, at least partially manufactured from the polymer composition as claimed in claim 1.

16. Polymer composition as claimed in claim 1, wherein the screening agent comprises a secondary alkylamine compound.

17. Polymer composition as claimed in claim 16, wherein the screening agent comprises a dicycloalkylamine compound.

* * * * *